US011300560B1

(12) United States Patent
Lo et al.

(10) Patent No.: US 11,300,560 B1
(45) Date of Patent: Apr. 12, 2022

(54) SYSTEM AND METHOD FOR SENSING CONCENTRATION OF MATTER

(71) Applicant: NATIONAL CHENG KUNG UNIVERSITY, Tainan (TW)

(72) Inventors: Yu-Lung Lo, Tainan (TW); Chieh-Chen Tsai, Taichung (TW)

(73) Assignee: National Cheng Kung University, Tainan (TW)

(*) Notice: Subject to any disclaimer, the term of this patent is extended or adjusted under 35 U.S.C. 154(b) by 0 days.

(21) Appl. No.: 17/100,964

(22) Filed: Nov. 23, 2020

(30) Foreign Application Priority Data

Sep. 30, 2020 (TW) .................................. 109134250

(51) Int. Cl.
| | | |
|---|---|---|
| *G01N 33/49* | (2006.01) | |
| *G01N 21/21* | (2006.01) | |
| *A61B 5/1455* | (2006.01) | |
| *A61B 5/145* | (2006.01) | |
| *G01N 21/31* | (2006.01) | |

(52) U.S. Cl.
CPC .......... *G01N 33/49* (2013.01); *A61B 5/1455* (2013.01); *A61B 5/14532* (2013.01); *A61B 5/14546* (2013.01); *G01N 21/21* (2013.01); *G01N 21/31* (2013.01)

(58) Field of Classification Search
CPC ........ G01N 33/49; G01N 21/31; G01N 21/21; A61B 5/1455; A61B 5/14546; A61B 5/14532
USPC ....................................................... 356/40
See application file for complete search history.

(56) References Cited

U.S. PATENT DOCUMENTS

| | | | | |
|---|---|---|---|---|
| 4,589,776 A | * | 5/1986 | Carver ................... | G01N 21/21 250/225 |
| 4,901,728 A | * | 2/1990 | Hutchison .......... | A61B 5/14558 356/368 |
| 5,321,265 A | * | 6/1994 | Block .................. | A61B 5/0059 250/339.02 |

(Continued)

FOREIGN PATENT DOCUMENTS

| | | |
|---|---|---|
| CN | 108351296 A | 7/2018 |
| TW | I627395 B | 6/2018 |
| TW | 201831882 A | 9/2018 |

OTHER PUBLICATIONS

Matthieu Dubreuil et al., "Snapshot Mueller matrix polarimeter by wavelength polarization coding," Optics Express, Oct. 17, 2007, pp. 13660-13668, vol. 15, No. 21.

(Continued)

*Primary Examiner* — Roy M Punnoose
(74) *Attorney, Agent, or Firm* — CKC & Partners Co., LLC (57) ABSTRACT

A system for sensing concentration is provided. A light source emits at least a light ray which passes through a first polarization state changing module and is directed to a biological tissue to generate a response light ray. The response light ray is received by a sensor after passing through a second polarization state changing module. A calculation circuit calculates a Muller matrix corresponding to the biological tissue according to the response light ray, and calculates a depolarization index of the biological tissue according to the Muller matrix, and calculates an optical path length according to the depolarization index, and calculates the concentration of matter of the biological tissue according to the optical path length.

10 Claims, 5 Drawing Sheets

(56) References Cited

U.S. PATENT DOCUMENTS

| | | | |
|---|---|---|---|
| 5,383,452 A * | 1/1995 | Buchert | A61B 5/14558 600/347 |
| 5,788,632 A * | 8/1998 | Pezzaniti | G01N 21/21 356/368 |
| 9,885,698 B2 | 2/2018 | Islam | |
| 10,188,332 B2 * | 1/2019 | Lo | A61B 5/0066 |
| 2018/0228415 A1 * | 8/2018 | Lo | A61B 5/14532 |
| 2020/0041410 A1 | 2/2020 | Ashrafi | |

OTHER PUBLICATIONS

American Diabetes Association, "Classification and Diagnosis of Diabetes," Diabetes care, Jan. 2017, pp. S11-S24, vol. 40, Supplement 1.

Sanghamitra Mandal, "Glucose Level Estimation Based on Invasive Electrochemical, and Non-Invasive Optical Sensing Methods," Thesis and Dissertations of University of Arkansas, Fayetteville, May 2018.

Sanghamitra Mandal et al., "An In-Vitro Optical Sensor Designed to Estimate Glycated Hemoglobin Levels," Sensors, Apr. 4, 2018, pp. 1-19, vol. 18(4):1084.

Jagjit Kaur et al., "Different strategies for detection of HbA1c emphasizing on biosensors and point-of-care analyzers," Biosensors and Bioelectronics, Jun. 7, 2018, pp. 85-100, vol. 123.

Shaivya Gupta et al., "Laboratory Diagnosis of HbA1c: A Review," Journal of Nanomedicine Research, Apr. 25, 2017, pp. 1-10, vol. 5, Issue 4.

Hiroyuki Fujiwara, "Chapter 4: Principles of Spectroscopic Ellipsometry", Spectroscopic Ellipsometry Principles and Applications, Mar. 2007, pp. 81-146.

Razvigor Ossikovski, "Differential matrix formalism for depolarizing anisotropic media," Optics Letters, Jun. 15, 2011, pp. 2330-2332, vol. 36, No. 12.

R. M. A. Azzam, "Propagation of partially polarized light through anisotropic media with or without depolarization: A differential 4x 4 matrix calculus," Journal of the Optical Society of America, Dec. 1978, pp. 1756-1767, vol. 68, No. 12.

Chia-Chi Liao, "Research on Using Interference with Broad-bandwidth Light in Near-field Optics and Mueller Optical Coherence Tomography," PhD Dissertation of National Cheng Kung University, Jul. 2013, Taiwan, R.O.C.

Emily Jane Gallagher et al., "Review of hemoglobin A1c in the management of diabetes," Journal of Diabetes, Mar. 4, 2009, pp. 9-17, vol. 1, Issue 1.

David M. Nathan et al., "Translating the A1C Assay Into Estimated Average Glucose Values," Diabetes Care, Aug. 2008, pp. 1473-1478, vol. 31, No. 8.

Rafat R. Ansari et al., "New optical scheme for a polarimetric-based glucose sensor," Journal of Biomedical Optics, Jan. 1, 2004, pp. 103-115, vol. 9(1).

Quoc-Hung Phan et al., "Stokes-Mueller matrix polarimetry system for glucose sensing," Optics and Lasers in Engineering, Sep. 1, 2016, pp. 120-128, vol. 92.

Quoc-Hung Phan et al., "Differential Mueller matrix polarimetry technique for non-invasive measurement of glucose concentration on human fingertip," Optics Express, Jun. 26, 2017, pp. 15179-15187, vol. 25, No. 13.

Yu-Jen Chang et al., "Full-Field Stokes-Mueller Matrix Imaging Polarimetry System Based on Electro-Optical Modulators," IEEE Photonics Journal, Dec. 2018, vol. 10, No. 6.

Tseng-Lin Chen et al., "Noninvasive measurement of glucose concentration on human fingertip by optical coherence tomography," Journal of Biomedical Optics, Apr. 10, 2018, pp. 047001-1-047001-9, vol. 23(4).

Li-Han Lin et al., "Optical detection of glucose concentration in samples with scattering particles," Applied optics, Dec. 10, 2015, pp. 10425-10431, vol. 54, No. 35.

Thi-Thu-Hien Pham et al., "Extraction of effective parameters of turbid media utilizing the Mueller matrix approach study of glucose sensing," Journal of Biomedical Optics, Sep. 6, 2012, pp. 097002-1-097002-15, vol. 17(9).

Alireza Molazemhosseini et al., "Single-Use Disposable Electrochemical Label-Free Immunosensor for Detection of Glycated Hemoglobin (HbA1c) Using Differential Pulse Voltammetry (DPV)," Sensors, Jul. 1, 2016, pp. 1-11, vol. 16 (7): 1024.

Ang Liu et al., "A New Electrochemical HbA1c Biosensor Based on Flow Injection and Screen-Printed Electrode," International Journal of Electrochemical Science, Mar. 1, 2016, pp. 3086-3094, vol. 11.

Seung Yeon Song et al., "Boronic acid-modified thin film interface for specific binding of glycated hemoglobin (HbA1c) and electrochemical biosensing," Sensors and Actuators B: Chemical, May 7, 2009, pp. 233-239, vol. 140.

Ko-Wei Chang et al., "An integrated microfluidic system for measurement of glycated hemoglobin Levels by using an aptamer-antibody assay on magnetic beads," Biosensors and Bioelectronics, Jan. 13, 2015, pp. 397-403, vol. 68.

Satoshi Yoshida et al., "Optical screening of diabetes mellitus using non-invasive Fourier-transform infrared spectroscopy technique for human lip," Journal of Pharmaceutical and Biomedical Analysis, Dec. 28, 2012, pp. 169-176, vol. 76.

CNOGA medical, "Cnoga Medical Hybrid Non-invasive Glucometer," https://cnogacare.co/hybridglucometer/, Dec. 2, 2019.

Dennis H. Goldstein, "Mueller matrix dual-rotating retarder polarimeter," Applied Optics, Nov. 1, 1992, pp. 6676-6683, vol. 31, No. 31.

Quoc-Hung Phan et al., "Surface plasmon resonance prism coupler for gas sensing based on Stokes polarimetry," Sensors and Actuators B: Chemical, Apr. 22, 2015, pp. 247-254, vol. 216.

Quoc-Hung Phan et al., "Stokes-Muller matrix polarimetry technique for circular dichroism/ birefringence sensing with scattering effects," Journal of Biomedical Optics, Apr. 6, 2017, pp. 047002-1-047002-8, vol. 22(4).

Quoc-Hung Phan et al., "Surface plasmon resonance prism coupler for enhanced circular dichroism sensing," Optics Express, Jun. 3, 2016, pp. 12812-12824, vol. 24, No. 12.

Quoc-Hung Phan et al., "Surface plasmon resonance prism coupler for enhanced circular birefringence sensing and application to non-invasive glucose detection," Optics Express, Aug. 17, 2020, pp. 24889-24899, vol. 28, No. 17.

* cited by examiner

| Concentration x(%) | Average absorbance Ae | I | I/I₀ | $-\ln(I/I_0)$ |
|---|---|---|---|---|
| Air | 3.2048 | 1.1284 | 1 | 0 |
| 2×10⁻⁵ | 3.4476 | 0.6842 | 0.60635 | 0.5 |
| 4×10⁻⁵ | 4.0099 | 0.5223 | 0.46287 | 0.77 |
| 6×10⁻⁵ | 4.753 | 0.3993 | 0.35386 | 1.039 |
| 8×10⁻⁵ | 5.3778 | 0.3228 | 0.2861 | 1.251 |

SYSTEM AND METHOD FOR SENSING CONCENTRATION OF MATTER

RELATED APPLICATIONS

This application claims priority to Taiwan Application Serial Number 109134250 filed Sep. 30, 2020, which is herein incorporated by reference.

BACKGROUND

Field of Invention

The present invention relates to a non-invasive method for sensing concentration of matter.

Description of Related Art

Diabetes is a major health care problem nowadays. The incidence rate is rising rapidly all over the world and has a huge economic impact. At present, many technologies have been proposed in the industry to detect diabetes by measuring the glucose concentration in human blood. Most of the glucose sensors on the market are based on invasive needles which cause fear of sharp objects, excessive pain, skin irritation, the risk of patient infection, and a large number of needle sticks may damage finger tissues. In recent years, the research focus of the field has shifted to the development of painless optical non-invasive technology. A variety of non-invasive technologies have been developed to directly detect glucose concentration using body tissues (fingertips, skin, tears and saliva).

Since 1980, the clinic has approved the measurement of glycosylated hemoglobin (HbA1c) in diabetic patients. The sugar in the blood is called glucose. When glucose binds to the hemoglobin of red blood cells, it is called glycosylated hemoglobin. A glycosylated hemoglobin test shows the patient's average blood glucose level in the last 3 months which is the life span of red blood cells. How to propose a non-invasive sensing method for glycosylated hemoglobin is a topic of concern to those skilled in the art.

SUMMARY

Embodiments of the present disclosure provide a system including at least one light source, a first polarization state changing module, a sensor, a second polarization state changing module and a calculation circuit. The light source is configured to emit a light ray. The first polarization state changing module is disposed between the light source and a biological tissue. The light ray is configured to pass through the first polarization state changing module and then directed to the biological tissue to generate at least one response light ray. The second polarization state changing module is disposed between the sensor and the biological tissue. The response light ray is configured to pass through the second polarization state changing module and then received by the sensor. The calculation circuit is communicatively connected to the sensor and configured to calculate at least one Muller matrix corresponding to the biological tissue according to the response light ray, calculate a depolarization index corresponding to the biological tissue according to the Muller matrix, calculate an optical path length according to the depolarization index, and calculate a concentration of a matter in the biological tissue according to the optical path length, in which the matter is configured to absorb at least a portion of the light ray.

In some embodiments, the calculation circuit calculates the optical path length according to the following equation (1).

$$\Delta = e^{-L/l} \qquad (1)$$

$\Delta$ is the depolarization index, L is a length of the biological tissue, and l is the optical path length.

In some embodiments, the light ray includes a first light ray with a first wavelength and a second light ray with a second wavelength. The response light ray includes a first response light ray and a second response light ray. The calculation circuit calculates the concentration of the matter according to the following equation (2).

$$\frac{I_{\lambda_1}}{I_{\lambda_2}} = e^{(\varepsilon_{\lambda_1} - \varepsilon_{\lambda_2}) l \cdot x} \qquad (2)$$

$I_{\lambda_1}$ is an intensity of the first response light ray, $I_{\lambda_2}$ is an intensity of the second response light ray, $\varepsilon_{\lambda_1}$ is a Molar absorption coefficient of the matter with respect to the first wavelength, $\varepsilon_{\lambda_2}$ is a Molar absorption coefficient of the matter with respect to the second wavelength, and x is the concentration of the matter.

In some embodiments, the light source is an adjustable light source configured to emit the first light ray and the second light ray at different time according to a control signal.

In some embodiments, the light ray has a first wavelength, and the calculation circuit calculates the concentration of the mater according to the following equation (3).

$$-\ln \frac{I_{\lambda_1}}{I_{o1}} = \varepsilon_{\lambda_1} \cdot l \cdot x \qquad (3)$$

$I_{o1}$ is an intensity of the light ray, $I_{\lambda_1}$ is an intensity of the response light ray, $\varepsilon_{\lambda_1}$ is a Molar absorption coefficient of the matter with respect to the first wavelength, and x is the concentration of the matter.

In some embodiments, the light ray has a first wavelength. The calculation circuit divides each element of the Muller matrix by an element at a first column and a first row of the Muller matrix to obtain a normalized matrix and calculate an average absorbance according to the Muller matrix and the normalized matrix. The calculation circuit calculates the concentration of the matter according to the following equation (4).

$$x = \frac{c_{\lambda_1} A e_{\lambda_1}}{\varepsilon_{\lambda_1} \cdot l} \qquad (4)$$

$\varepsilon_{\lambda_1}$ is a Molar absorption coefficient of the matter with respect to the first wavelength, $c_{\lambda_1}$ is a ratio constant corresponding to the first wavelength, $Ae_{\lambda_1}$ is the average absorbance, and x is the concentration of the matter.

In some embodiments, the at least one light ray includes a first light ray with a first wavelength and a second light ray with a second wavelength. The calculation circuit calculates two normalized matrices according to a first Muller matrix and a second Muller matrix so as to calculate an average absorbance corresponding to the first wavelength and an average absorbance corresponding to the second wavelength. The calculation circuit calculates the concentration of the matter according to the following equation (5).

$$x = \frac{c_{\lambda_1} Ae_{\lambda_1} - c_{\lambda_2} Ae_{\lambda_2}}{(\varepsilon_{\lambda_1} - \varepsilon_{\lambda_2}) \cdot l} \quad (5)$$

$\varepsilon_{\lambda_1}$ is a Molar absorption coefficient of the matter respect to the first wavelength, $\varepsilon_{\lambda_2}$ is a Molar absorption coefficient of the matter respect to the second wavelength, $c_{\lambda_1}$ is a ratio constant corresponding to the first wavelength, $c_{\lambda_2}$ is a ratio constant corresponding to the second wavelength, $Ae_{\lambda_1}$ is the average absorbance of the first wavelength, $Ae_{\lambda_2}$ is the average absorbance of the second wavelength, and x is the concentration of the matter.

In some embodiments, the sensor is a Charge-coupled Device (CCD) sensor or a Complementary Metal-Oxide Semiconductor (CMOS) sensor, and the system is a wearable device.

In some embodiments, the matter is glycosylated hemoglobin or glucose.

From another aspect, embodiments of the present disclosure provide a method for a system including a calculating circuit. The method includes: emitting, by at least one light source, a light ray which is configured to pass through a first polarization state changing module and then directed to a biological tissue to generate at least one response light ray which is configured to pass through a second polarization state changing module and then received by a sensor; calculating at least one Muller matrix corresponding to the biological tissue according to the response light ray; calculating a depolarization index corresponding to the biological tissue according to the Muller matrix; calculating an optical path length according to the depolarization index; and calculating a concentration of a matter in the biological tissue according to the optical path length, in which the matter is configured to absorb at least a portion of the light ray.

In the above-mentioned system and method, the concentration of a matter in the biological tissue can be measured in a non-invasive manner, and the volume of the system can be reduced to implement a wearable device.

BRIEF DESCRIPTION OF THE DRAWINGS

The invention can be more fully understood by reading the following detailed description of the embodiment, with reference made to the accompanying drawings as follows.

DETAILED DESCRIPTION

Specific embodiments of the present invention are further described in detail below with reference to the accompanying drawings, however, the embodiments described are not intended to limit the present invention and it is not intended for the description of operation to limit the order of implementation. Moreover, any device with equivalent functions that is produced from a structure formed by a recombination of elements shall fall within the scope of the present invention. Additionally, the drawings are only illustrative and are not drawn to actual size.

The using of "first", "second", "third", etc. in the specification should be understood for identifying units or data described by the same terminology, but are not referred to particular order or sequence.

Figure 1:
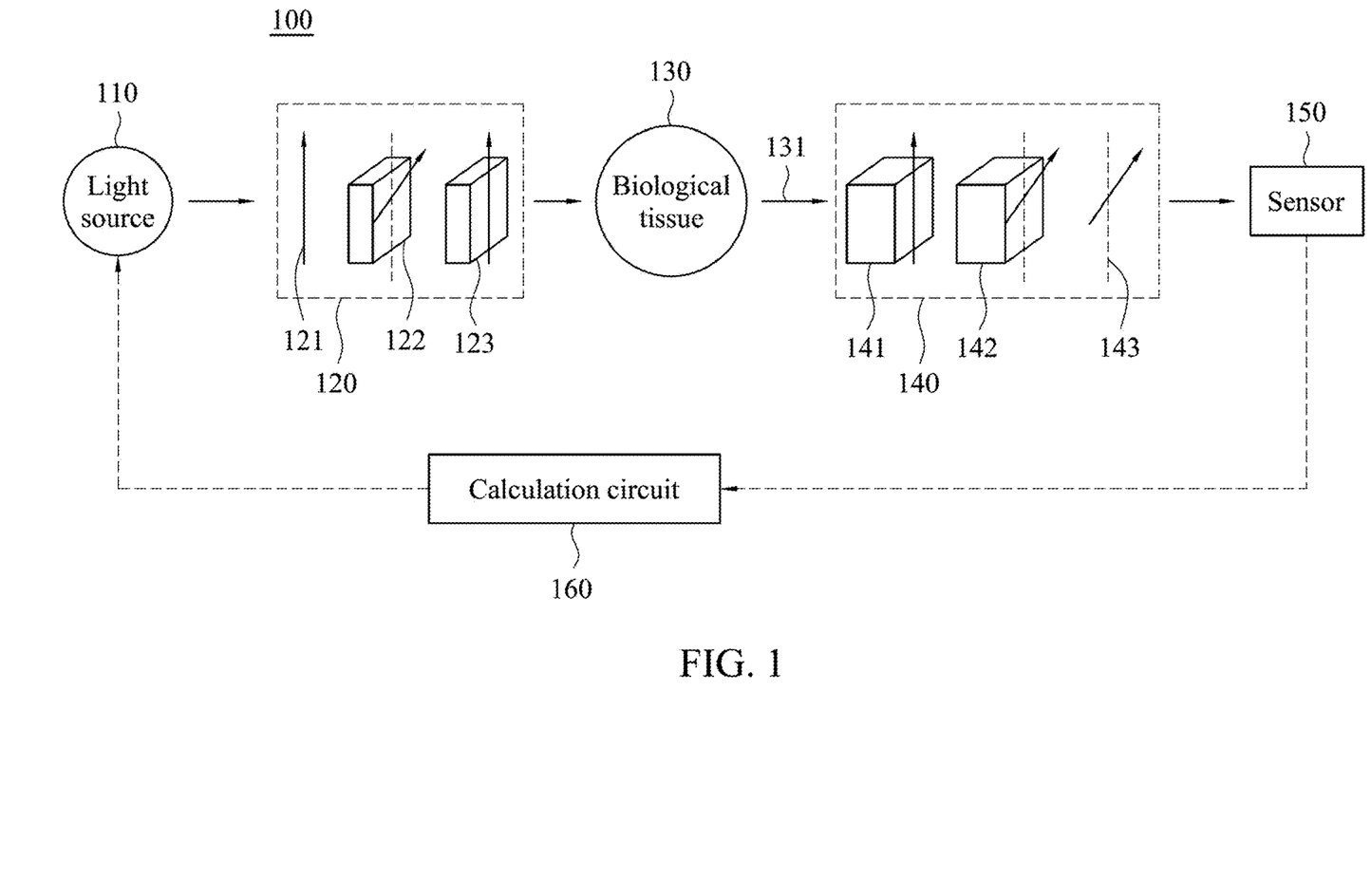
FIG. 1 a schematic diagram of a system in accordance with an embodiment.

FIG. 1 a schematic diagram of a system in accordance with an embodiment. A system 100 includes a light source 110, a first polarization state changing module 120, a second polarization state changing module 140, a sensor 150 and a calculation circuit 160. The first polarization state changing module 120 is disposed between the light source 110 and the biological tissue 130. The second polarization state changing module 140 is disposed between the biological tissue 130 and the sensor 150.

The light source 110 provides light rays with particular wavelengths. In some embodiments, the light source 110 emits a broad-spectrum light ray. In some embodiments, the light source 110 is an adjustable light source for emitting light rays with different wavelengths at different time according to a control signal. In some embodiments, there are more than one light sources 110, and each of the light sources emits a light ray with a particular wavelength at different time or at the same time. The light source 110 may be any suitable laser or light emitting diode.

The first polarization state changing module 120 changes a polarization state of the light ray. In the embodiment, the first polarization state changing module 120 includes a linear polarizer 121, birefringent plats 122 and 123. The angle of the linear polarizer 121 is 0 degree. The optical axis of the birefringent plat 122 is 45 degrees. The optical axis of the birefringent plat 123 is 0 degree. The first polarization state changing module 120 may be referred to as a polarization state generator (PSG).

The biological tissue 130 may be fingertips, skin of any part, tears and saliva, etc. that is not limited in this disclosure. The light ray passes through the first polarization state changing module 120 and then is directed to the biological tissue 130 to generate a response light ray 131 which may be a reflected light ray or a penetrating light ray. In the embodiments, the aim is to sense a concentration of a matter in the biological tissue 130 in which the matter absorbs at least a portion of the light ray. In the embodiment, the matter is glycosylated hemoglobin, but the matter may be glucose or anything that absorbs light.

The second polarization state changing module 140 includes birefringent plats 141 and 142 and a linear polarizer 143. The optical axis of the birefringent plat 141 is 0 degree. The optical axis of the birefringent plat 142 is 45 degrees. The angle of the linear polarizer 143 is 90 degrees. The material of the birefringent plats 141 and 142 is identical to that of the birefringent plats 122 and 123. In some embodiments, the thickness of the birefringent plats 141 and 142 is greater than that of the birefringent plats 122 and 123. For example, the thickness of the birefringent plats 141 and 142 is the same and is 5 times of the thickness of the birefringent plats 122 and 123. The second polarization state changing module 140 may be referred to as a polarization state analyzer (PSA). In some embodiments, the first polarization state changing module 120 and the second polarization state changing module 140 may include any device capable of changing the polarization state of light. For example, they may include liquid crystal, photoelectric modulator, pressure modulator, magnetic modulator, etc.

The sensor 150 may be a Charge-coupled Device (CCD) sensor or a Complementary Metal-Oxide Semiconductor (CMOS) sensor. The mentioned response light ray 131 passes through the second polarization state changing module 140 and then is received by the sensor 150 which can measure an intensity of the response light ray.

The calculation circuit 160 may be a controller, a processor, a circuit, a computer or a server. The calculation circuit 160 is communicatively connected to the light source 110 and the sensor 150 in a wire or wireless way. The calculation circuit 160 also receives data of the sensor 150. The calculation circuit 160 calculates a Muller matrix corresponding to the biological tissue 130 according to the intensity of the response light ray, for example, by the reference of DUBREUIL, Matthieu, et al. "Snapshot Mueller matrix polarimeter by wavelength polarization coding". Optics express, 2007, 15.21: 13660-13668. However, the Muller matrix may be calculated based on other snapshot technology, and the first polarization state changing module 120 and the second polarization state changing module 140 may be adjusted correspondingly (e.g. disposing the polarizer or the birefringent plat in different angle or in different order). The following describes how to calculate the glycosylated hemoglobin concentration based on the intensity of response light ray and the Muller matrix.

Stokes vector and Mueller matrix have to be described first. One Stokes vector has four parameters generally represented as $S_0$, $S_1$, $S_2$, and $S_3$. The parameter $S_0$ indicates the sum of the power of the electric fields of the light ray (i.e. a type of electromagnetic wave) along two orthogonal directions. The parameter $S_1$ indicates the difference of the power of the electric fields along the two orthogonal directions. The parameters $S_2$, $S_3$ are used to provide information of the polarization angle and the state of the circular polarization. The person in the art should be able to understand the definition of Stokes vector, and therefore it will not be described in detail.

A general optical sampling is represented as $S_{out}=M \times S_{in}$, where $S_{in}$ is the Stokes vector of the light ray emitted to the biological tissue, and $S_{out}$ is the Stokes vectors of the response light ray reflected or penetrating from the biological tissue. The optical properties of the biological tissue can be represented as a Mueller matrix M (also referred to as a macroscopic Mueller matrix) as the following equation (1).

$$S_{out} = \begin{bmatrix} M_{11} & M_{12} & M_{13} & M_{14} \\ M_{21} & M_{22} & M_{23} & M_{24} \\ M_{31} & M_{32} & M_{33} & M_{34} \\ M_{41} & M_{42} & M_{43} & M_{44} \end{bmatrix} \times S_{in} \quad (1)$$

The Mueller matrix M may be transformed into one or more differential Mueller matrices to describing different optical properties. It is assumed that the light ray propagates along the z-axis of a right-handed Cartesian coordinate system. The differential Mueller matrix is thus given by the following equation (2).

$$m = (dM/dz)M^{-1} \quad (2)$$

m represents the differential Mueller matrix. The eigenvectors of the Mueller matrix M and the differential Mueller matrix m are represented as $V_M$ and $V_m$, respectively. The eigenvalues of the Mueller matrix M and the differential Mueller matrix m are represented as $\lambda_M$ and $\lambda_m$, respectively. Assume that the initial condition matrix Mueller matrix $M_{z=0}$ has the form of an identity matrix. The eigenvalues $\lambda_M$ and $\lambda_m$ are related as the following equation (3), and thus the eigenvalues $\lambda_m$ can be calculated after the eigenvalues $\lambda_M$ are obtained.

$$\lambda_m = \ln(\lambda_M)/Z \quad (3)$$

Assuming that $m_\lambda$ is a diagonal matrix with diagonal elements of eigenvalues $\lambda_m$, the differential Mueller matrix m can be obtained from an eigen analysis of the Mueller matrix M as the following equation (4).

$$m = V_M m_\lambda V_M^{-1} = \begin{bmatrix} m_{11} & m_{12} & m_{13} & m_{14} \\ m_{21} & m_{22} & m_{23} & m_{24} \\ m_{31} & m_{32} & m_{33} & m_{34} \\ m_{41} & m_{42} & m_{43} & m_{44} \end{bmatrix} \quad (4)$$

In accordance with the analysis of the differential Mueller matrix, a general anisotropic sample can be partitioned into 16 different elements, with each element describing a different aspect of the basic optical behavior. Let $M_{LB}$, $M_{CB}$, $M_{LD}$, and $M_{CD}$ be the macroscopic Mueller matrices describing the linear birefringence (LB), circular birefringence (CB), linear dichroism (LD) and circular dichroism (CD) properties. A differential matrix $m_{BD}$ of a composite sample with LB, CB, LD, and CD optical properties can be expressed as the following equation (5).

$$\frac{1}{d}\begin{bmatrix} \ln\left[(1-R^2)\sqrt{\frac{1-D}{1+D}}\right] & -\ln\sqrt{\frac{1-D}{1+D}}\cos(2\theta_d) & -\ln\sqrt{\frac{1-D}{1+D}}\sin(2\theta_d) & \ln\left(\frac{1+R}{1-R}\right) \\ -\ln\sqrt{\frac{1-D}{1+D}}\cos(2\theta_d) & \ln\left[(1-R^2)\sqrt{\frac{1-D}{1+D}}\right] & 2\gamma & -\beta\sin(2\alpha) \\ -\ln\sqrt{\frac{1-D}{1+D}}\sin(2\theta_d) & -2\gamma & \ln\left[(1-R^2)\sqrt{\frac{1-D}{1+D}}\right] & \beta\cos(2\alpha) \\ \ln\left(\frac{1+R}{1-R}\right) & \beta\sin(2\alpha) & -\beta\cos(2\alpha) & \ln\left[(1-R^2)\sqrt{\frac{1-D}{1+D}}\right] \end{bmatrix} \quad (5)$$

In the equation (5), d is the sample thickness; $\alpha$ and $\beta$ are the orientation angle and phase retardation of the LB property, respectively; $\gamma$ is the optical rotation angle of the CB property; $\theta_d$ and D are the orientation angle and linear dichroism of the LD property, respectively; and R is the circular amplitude anisotropy of the CD property (i.e. $R=(r_R-r_L)/(r_R+r_L)$, $-1 \leq R \leq +1$, were $r_R$ and $r_L$ are the absorptions of right-hand circular polarized light and left-hand circular polarized light, respectively).

The differential Mueller matrix describing the depolarization effect in depolarizing anisotropic media is expressed as the following equation (6).

$$m_\Delta = \frac{1}{d}\begin{bmatrix} 0 & k'_q & k'_u & k'_v \\ -k'_q & -k'_{iq} & \eta'_v & \eta'_u \\ -k'_u & \eta'_v & -k'_{iu} & \eta'_q \\ -k'_v & \eta'_u & \eta'_q & -k'_{iv} \end{bmatrix} \quad (6)$$

The diagonal depolarization is characterized by the parameters $K'_{iq}$, $K'_{iu}$, and $K'_{iv}$. The anomalous dichroism and anomalous depolarization are characterized by the parameters $K'_{q,u,v}$ and $\eta'_{q,u,v}$.

The differential Mueller matrix describing all of the LB, CB, LD, CD and Dep properties of an anisotropic optical sample can be obtained by summing equations (5), and (6) as the following equation (7).

$$m_{BD\Delta} = m_{BD} + m_\Delta = \quad (7)$$

$$\frac{1}{d}\begin{bmatrix} \ln\left[(1-R^2)\sqrt{\frac{1-D}{1+D}}\right] & -\ln\sqrt{\frac{1-D}{1+D}}\cos(2\theta_d)+k'_q & -\ln\sqrt{\frac{1-D}{1+D}}\sin(2\theta_d)+k'_u & \ln\left(\frac{1+R}{1-R}\right)+k'_v \\ -\ln\sqrt{\frac{1-D}{1+D}}\cos(2\theta_d)-k'_q & \ln\left[(1-R^2)\sqrt{\frac{1-D}{1+D}}\right]-k'_{iq} & 2\gamma+\eta'_v & -\beta\sin(2\alpha)+\eta'_u \\ -\ln\sqrt{\frac{1-D}{1+D}}\sin(2\theta_d)-k'_u & -2\gamma+\eta'_v & \ln\left[(1-R^2)\sqrt{\frac{1-D}{1+D}}\right]-k'_{iu} & \beta\cos(2\alpha)+\eta'_q \\ \ln\left(\frac{1+R}{1-R}\right)-k'_v & \beta\sin(2\alpha)+\eta'_u & -\beta\cos(2\alpha)+\eta'_q & \ln\left[(1-R^2)\sqrt{\frac{1-D}{1+D}}\right]-k'_{iv} \end{bmatrix}$$

In operation, the macroscopic Mueller matrix M can be determined from the equation (1), and the differential Mueller matrix can be calculated by using the equation (4). The optical parameters describing the anisotropic behavior of the sample can be obtained by equating the differential Mueller matrix of the equation (4) with that of the equation (7). By doing so, the orientation angle $\alpha$, phase retardation $\beta$, optical rotation angle $\gamma$, orientation angle $\theta_d$, linear dichroism D and circular dichroism R can be obtained respectively as the following equations (8)-(13).

$$\alpha = \frac{1}{2}\tan^{-1}\left(\frac{m_{42}-m_{24}}{m_{34}-m_{43}}\right) \quad (8)$$

$$\beta = \sqrt{\left[\frac{(m_{42}-m_{24})}{2}\right]^2 + \left[\frac{(m_{34}-m_{43})}{2}\right]^2} \quad (9)$$

$$\gamma = \frac{(m_{23}-m_{32})}{4} \quad (10)$$

$$\theta_d = \frac{1}{2}\tan^{-1}\left(\frac{m_{13}+m_{31}}{m_{12}+m_{21}}\right) \quad (11)$$

$$D = \frac{1-e^{-2\sqrt[2]{[m_{12}+m_{21}]^2+[m_{13}+m_{31}]^2}}}{1+e^{-2\sqrt[2]{[m_{12}+m_{21}]^2+[m_{13}+m_{31}]^2}}} \quad (12)$$

$$R = \frac{e^{\left(\frac{m_{14}-m_{41}}{2}\right)}-1}{e^{\left(\frac{m_{14}-m_{41}}{2}\right)}+1} \quad (13)$$

Similarly, the differential Mueller matrix describing the depolarization effect can be obtained by the following equation (14).

$$m_\Delta = \begin{bmatrix} 0 & \frac{(m_{12}-m_{21})}{2} & \frac{(m_{13}-m_{31})}{2} & \frac{(m_{14}-m_{41})}{2} \\ \frac{(m_{21}-m_{12})}{2} & m_{22}-m_{11} & \frac{(m_{23}-m_{32})}{2} & \frac{(m_{24}-m_{42})}{2} \\ \frac{(m_{31}-m_{13})}{2} & \frac{(m_{23}-m_{32})}{2} & m_{33}-m_{11} & \frac{(m_{34}-m_{43})}{2} \\ \frac{(m_{41}-m_{14})}{2} & \frac{(m_{24}-m_{42})}{2} & \frac{(m_{34}-m_{43})}{2} & m_{44}-m_{11} \end{bmatrix} \quad (14)$$

By performing inverse differential calculation on the differential matrix $m_\Delta$ in accordance with the equation (4), a macroscopic Mueller matrix $M_\Delta$ is obtained as the following equation (15).

$$M_\Delta = \begin{bmatrix} 1 & K_{12} & K_{13} & K_{14} \\ -K_{12} & K_{22} & K_{23} & K_{24} \\ -K_{13} & K_{23} & K_{33} & K_{34} \\ -K_{14} & K_{24} & K_{34} & K_{44} \end{bmatrix} \quad (15)$$

$K_{22}$ and $K_{33}$ are degrees of linear depolarization, and $K_{44}$ is the degree or circular depolarization. In general, the degree of depolarization is quantified by a depolarization index $\Delta$. When the value of the depolarization index $\Delta$ is 0, it indicates a non-depolarizing sample; and when the value is 1, it indicates an ideal depolarizer. The depolarization index $\Delta$ is expressed as the following equation (16).

$$\Delta = 1 - \sqrt{\frac{K_{22}^2 + K_{33}^2 + K_{44}^2}{3}} \qquad (16)$$

Next, an optical path length is calculated according to the depolarization index. The optical path length is represented as l, and the length of the biological tissue 130 is represented as L. Some light rays may pass through the sample without undergoing bulk scattering. The fraction of "unscattered" rays (or the depolarization index) can be determined from the fact that rays which travel a distance x within the sample have an integrated probability of having been scattered given by the following equation (17).

$$p(x) = 1 - e^{-x/l} \qquad (17)$$

Thus, the integrated probability of a light ray travelling the distance x within the sample and not undergoing scattering is given by the following equation (18).

$$1 - p(x) = e^{-x/l} \qquad (18)$$

Setting x=L, we find that the probability of a ray traveling through the full sample and not being scattered is as the following equation (19). That is, the optical path length (l) is obtained by substituting the depolarization index into the equation (19).

$$\Delta = e^{-L/l} \qquad (19)$$

Next, the concentration of glycosylated hemoglobin is calculated according to the response light ray and the optical path length. To be specific, the concentration of glycosylated hemoglobin is related to absorbance of the light ray, especially sensitive to the wavelengths 535 nanometers (nm) and 595 nm. The calculation formula is derived from the definition of the absorbance. In some embodiments, the light source 110 can emit a first light ray with a first wavelength and a second light ray with a second wavelength in which the first wavelength is, for example but not limited to, 535 nm and the second wavelength is 595 nm in the embodiment. An intensity of the first light ray is represented as $I_{o1}$. An intensity of the second light ray is represented as $I_{o2}$. In addition, an intensity of a first response light ray corresponding to the first wavelength is represented as $I_{\lambda_1}$. An intensity of the second response light ray corresponding to the second wavelength is represented as $I_{\lambda_2}$. An absorbance corresponding to the first wavelength is $A_{\lambda_1}$ defined in the following equation (20). An absorbance corresponding to the second wavelength is $A_{\lambda_1}$ defined in the following equation (21).

$$A_{\lambda_1} = -\ln\frac{I_{\lambda_1}}{I_{o1}} = \varepsilon_{\lambda_1} \cdot l \cdot x \qquad (20)$$

$$A_{\lambda_2} = -\ln\frac{I_{\lambda_2}}{I_{o2}} = \varepsilon_{\lambda_2} \cdot l \cdot x \qquad (21)$$

$\varepsilon_{\lambda_1}$ is a Molar absorption coefficient of the glycosylated hemoglobin with respect to the first wavelength. $\varepsilon_{\lambda_2}$ is a Molar absorption coefficient of the glycosylated hemoglobin with respect to the second wavelength. x is the concentration of the glycosylated hemoglobin. The intensity $I_{o1}$ of the first light ray is set to be equal to the intensity $I_{o2}$ of the second light ray, and therefore a ratio of the intensity $I_{\lambda_1}$ of the first response light ray to the intensity $I_{\lambda_2}$ of the second response light ray is represented as the following equation (22).

$$\frac{I_{\lambda_1}}{I_{\lambda_2}} = \frac{-I_{o1}e^{A_{\lambda_1}}}{-I_{o2}e^{A_{\lambda_2}}} = e^{(A_{\lambda_1} - A_{\lambda_2})} = e^{(\varepsilon_{\lambda_1} - \varepsilon_{\lambda_2})l \cdot x} \qquad (22)$$

In other words, the concentration x of the glycosylated hemoglobin is obtained by substituting the intensities $I_{\lambda_1}$ and $I_{\lambda_2}$, the optical path length l and the Molar absorption coefficients $\varepsilon_{\lambda_1}$ and $\varepsilon_{\lambda_2}$ into the equation (22).

The ratio of the intensities of the response light rays is used in the above embodiment, and thus no need to obtain the intensities $I_{o1}$ and $I_{o2}$. In other embodiments, the light source 110 emits a single light ray having an intensity $I_{o1}$ with a particular wavelength, and the calculation circuit 160 can obtain the intensity $I_{o1}$ according to the control signal which is send to the light source 110. The concentration x is obtained by substituting the intensity $I_{o1}$, the intensity $I_{\lambda_1}$ of the response light ray, the optical path length l and the Molar absorption coefficient $\varepsilon_{\lambda_1}$ into the equation (20).

The above embodiment adopts the definition of absorbance, and scattering and reflection are not considered. In the following embodiments, the Muller matrix is used to calculate required parameters. First, referring to the following equation (23) and (24), H is a matrix of optical parameters where LD, CD, CB, and LB represent linear dichroism, circular dichroism, circular birefringence and linear birefringence respectively. Ae is an average absorbance. In other words, the Muller matrix M has parameters of the absorbance.

$$M = e^{-H} \qquad (23)$$

$$H = \begin{bmatrix} Ae & -LD' & -CD & LD \\ LD' & Ae & LB & CB \\ -CD & -LB & Ae & LB' \\ LD & -CB & -LB' & Ae \end{bmatrix} \qquad (24)$$

The equation (23) can be rewritten into the following equation (25) via Taylor expansion where F is a normalized Muller matrix M by dividing all elements of the Muller matrix M by the element $M_{11}$ at the first column and the first row such that $M_{11}=1$ in the normalized matrix F. An equation (26) is derived from the equation (25) where det( ) is determinant of the matrix. That is to say, the average absorbance Ae is calculated according to the Muller matrix M and the normalized matrix F. Here, the order of the Taylor expansion can be determined according to the requirements of accuracy, and the higher the order, the smaller the error.

$$M = e^{-Ae}\left(I - F + \frac{1}{2}F^2 - \frac{1}{3!}F^3 + \frac{1}{4!}F^4 \ldots\right) \qquad (25)$$

$$Ae = \det\left(\ln\left(I - F + \frac{1}{2}F^2 - \frac{1}{3!}F^3 + \frac{1}{4!}F^4 \ldots\right)\right) - \det(\ln M) \qquad (26)$$

Figure 3:
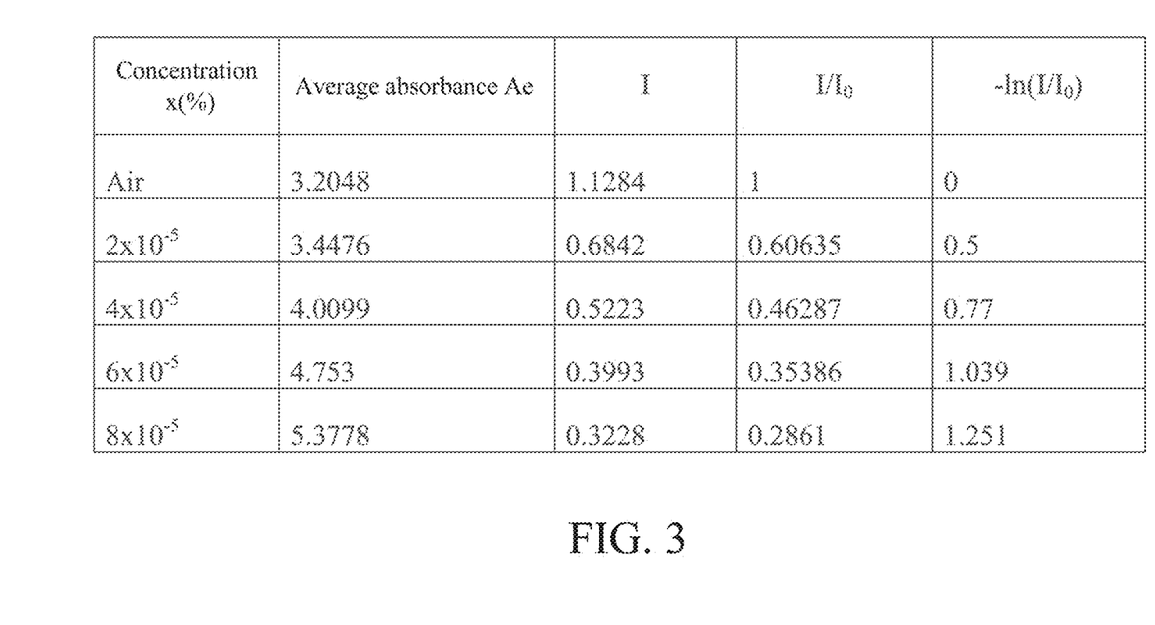
FIG. 3 is a diagram illustrating a table of experiment results in accordance with an embodiment.
Figure 4:
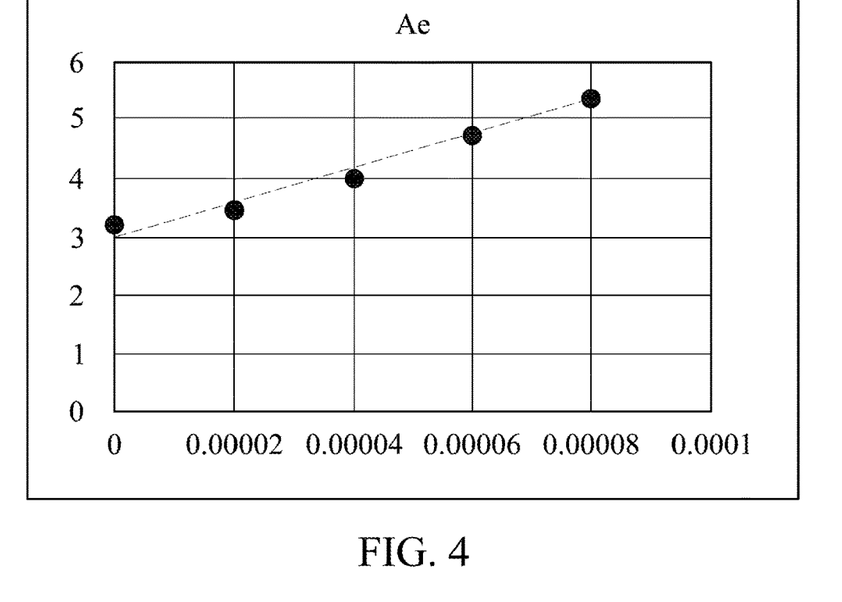
FIG. 4 and FIG. 5 are diagrams of experiment results in accordance with some embodiments.
Figure 5:
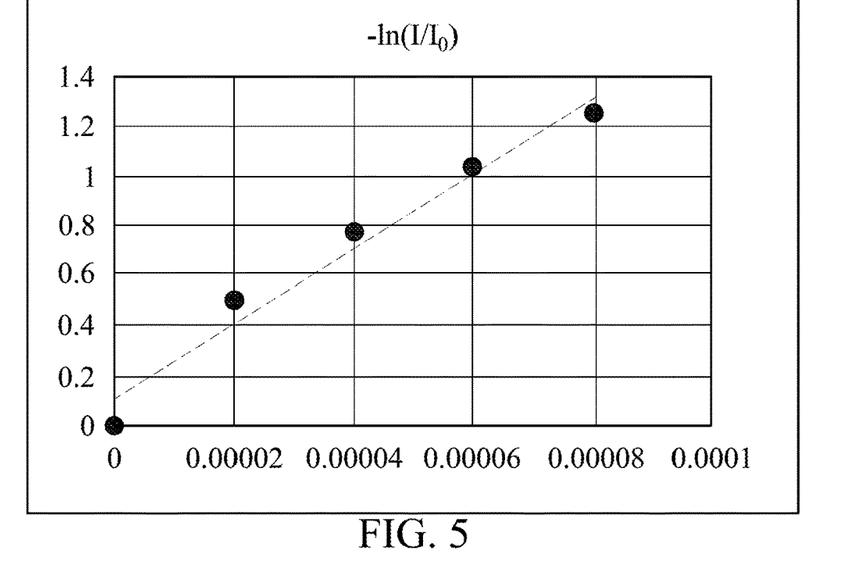

FIG. 3 is a diagram illustrating a table of experiment results in accordance with an embodiment. FIG. 4 and FIG. 5 are diagrams of experiment results in accordance with some embodiments. Herein, a sample with known concentration is obtained, and the average absorbance Ae is calculated according to the aforementioned method to illustrate the feasibility of this method. In FIG. 3, I is the intensity of input light ray, $I_0$ is the intensity of the response light ray. In FIG. 4, the horizontal axis is the concentration and the vertical axis is the average absorbance that is illustrated based on the first column and the second column of FIG. 3. The concentration is basically linear to the average absorbance. In FIG. 5, the horizontal axis is the concentration and the vertical axis is $-\ln(I/I_0)$ that is illustrated based on the first column and last column of FIG. 3. The concentration is also linear to $-\ln(I/I_0)$ basically. When the wavelength of the light ray is $\lambda_n$, the average absorbance calculated through Muller matrix is represented as $Ae_{\lambda_n}$. The absorbance calculated through intensities of light is represented as $A_{\lambda_n}$. The average absorbance is not equal to the absorbance $A_{\lambda_n}$, but there is a proportional relationship as the following equation (27) where n is a positive integer.

$$A_{\lambda_n} = c_{\lambda_n} Ae_{\lambda_n} \qquad (27)$$

$c_{\lambda_n}$ is a ratio constant which may be determined by experiments. As a result, the equation (22) can be rewritten into the following equation (28).

$$\frac{I_{\lambda_1}}{I_{\lambda_2}} = \frac{-I_{o1}e^{A_{\lambda_1}}}{-I_{o2}e^{A_{\lambda_2}}} = e^{(A_{\lambda_1} - A_{\lambda_2})} = e^{(c_{\lambda_1} Ae_{\lambda_1} - c_{\lambda_2} Ae_{\lambda_2})} = e^{(\varepsilon_{\lambda_1} - \varepsilon_{\lambda_2})lx} \qquad (28)$$

In other words, two Muller matrices M are calculated based on the first light ray and the second light ray respectively. Two normalized matrices are calculated based on these Muller matrices to calculate two average absorbance $Ae_{\lambda_1}$ and $Ae_{\lambda_2}$. These two average absorbance, corresponding ratio constants $c_{\lambda_1}$, $c_{\lambda_2}$, the optical path length l, and Molar absorption coefficients $\varepsilon_{A_1}$, $\varepsilon_{A_2}$ are substituted into the equation (28) to obtain the concentration x of glycosylated hemoglobin as the following equation (29).

$$x = \frac{\ln I_{\lambda_1} - \ln I_{\lambda_2}}{(\varepsilon_{\lambda_1} - \varepsilon_{\lambda_2}) \cdot l} = \frac{c_{\lambda_1} Ae_{\lambda_1} - c_{\lambda_2} Ae_{\lambda_2}}{(\varepsilon_{\lambda_1} - \varepsilon_{\lambda_2}) \cdot l} \qquad (29)$$

In some embodiments, the concentration may be calculated based on a single wavelength as the following equation (30).

$$x = \frac{\ln I_{o1} - \ln I_{\lambda_1}}{\varepsilon_{\lambda_1} \cdot l} = \frac{c_{\lambda_1} Ae_{\lambda_1}}{\varepsilon_{\lambda_1} \cdot l} \qquad (30)$$

In some embodiments, the first polarization state changing module 120 and the second polarization state changing module 140 only includes passive devices which are not driven by control singles. Therefore, the volume of the system 100 can be reduced. In some embodiments, the system 100 is a wearable device such as a smart bracelet, a smart watch, or an electrical device with any appearance which is not limited in the disclosure.

Figure 2A:
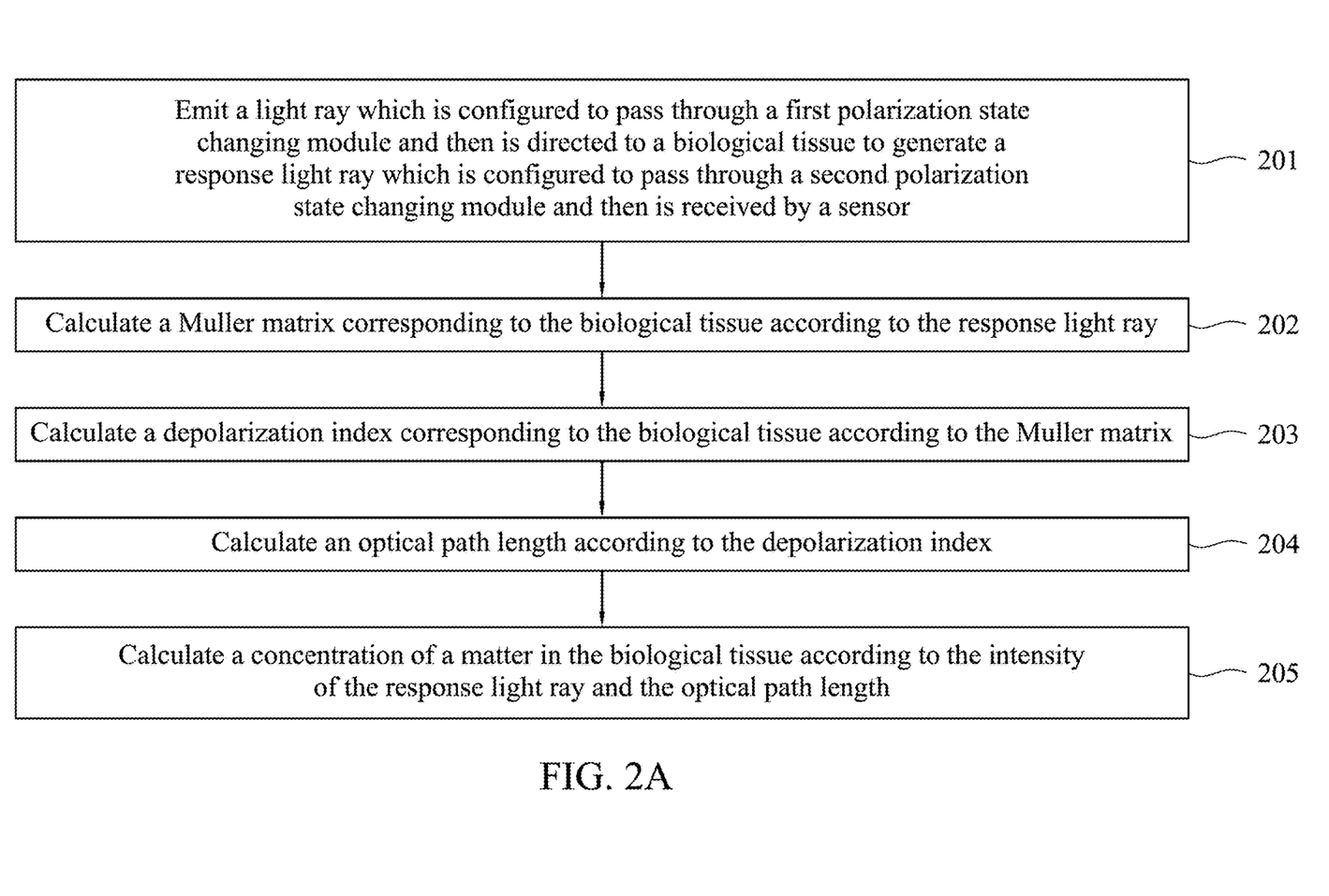
FIG. 2A is a flow chart of a method in accordance with an embodiment.

FIG. 2A is a flow chart of a method in accordance with an embodiment. Referring to 2A, in step 201, at least one light ray is emitted by at least one light source. The light ray is configured to pass through a first polarization state changing module and then is directed to a biological tissue to generate a response light ray which is configured to pass through a second polarization state changing module and then is received by a sensor. In step 202, a Muller matrix corresponding to the biological tissue is calculated according to the response light ray. In step 203, a depolarization index corresponding to the biological tissue is calculated according to the Muller matrix. In 204, an optical path length is calculated according to the depolarization index. In step 205, a concentration of a matter in the biological tissue is calculated according to the intensity of the response light ray and the optical path length.

Figure 2B:
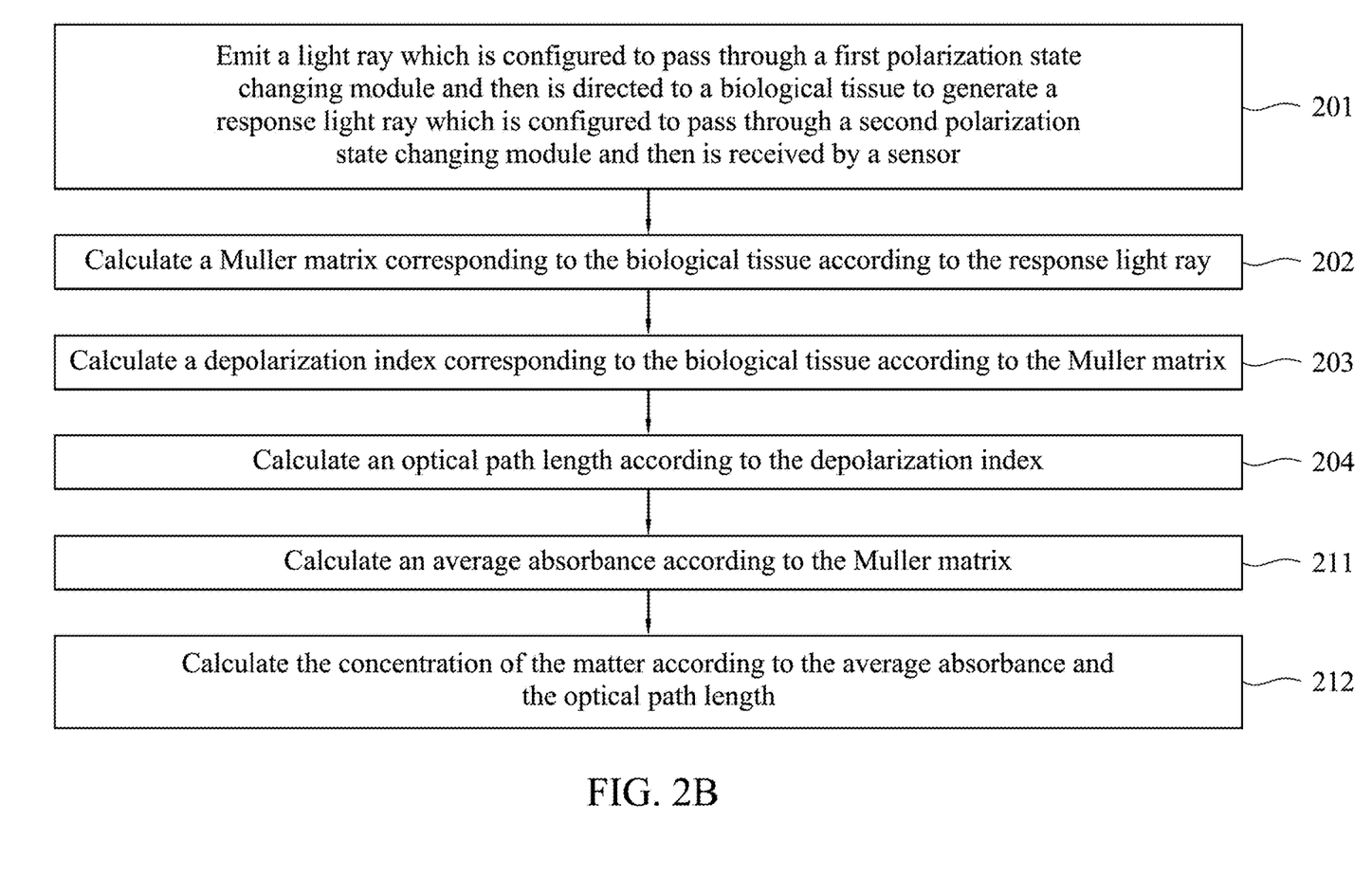
FIG. 2B is a flow chart of a method in accordance with an embodiment.

FIG. 2B is a flow chart of a method in accordance with an embodiment. Referring to FIG. 2, the steps 201 to 204 have been described above. In 211, an average absorbance is calculated according to the Muller matrix. In 212, the concentration of the matter is calculated according to the average absorbance and the optical path length. What FIG. 2A has in common with FIG. 2B is that the concentration of matter is calculated based on the optical path length.

All the steps in FIGS. 2A and 2B have been described in detail above with detailed equations, and therefore the description will not be repeated. Note that the steps in FIGS. 2A and 2B can be implemented as program codes or circuits, and the disclosure is not limited thereto. In addition, the method in FIGS. 2A and 2B can be performed with the aforementioned embodiments, or can be performed independently. In other words, other steps may be inserted between the steps of the FIGS. 2A and 2B.

In the above system and method, the concentration of the matter in the biological tissue can be calculated in a non-invasive manner. The concentration calculated based on the depolarization index is more accurate. In some embodiments, the volume of the system can also be reduced to implement a wearable device.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A system comprising:
    at least one light source configured to emit at least one light ray;
    a first polarization state changing module disposed between the at least one light source and a biological tissue, wherein the first polarization state changing module comprises at least one first birefringent plat and at least one first linear polarizer, and the at least one light ray is configured to pass through the first polarization state changing module and then directed to the biological tissue to generate at least one response light ray;
    a sensor;
    a second polarization state changing module disposed between the sensor and the biological tissue, wherein the second polarization state changing module comprises at least one second birefringent plat and at least one second linear polarizer, and the at least one response light ray is configured to pass through the second polarization state changing module and then received by the sensor; and
    a calculation circuit communicatively connected to the sensor and configured to calculate at least one Muller matrix corresponding to the biological tissue according to the at least one response light ray, calculate a depolarization index corresponding to the biological tissue according to the at least one Muller matrix, calculate an optical path length according to the depolarization index, and calculate a concentration of a matter in the biological tissue according to the optical path length, wherein the matter is configured to absorb at least a portion of the at least one light ray, wherein the sensor is a Charge-coupled Device (CCD) sensor or a Complementary Metal-Oxide Semiconductor (CMOS) sensor, and the system is a wearable device.

2. The system of claim 1, wherein the calculation circuit is configured to calculate the optical path length according to an equation (1), $$\Delta = e^{-L/l} \qquad (1)$$

wherein $\Delta$ is the depolarization index, L is a length of the biological tissue, and l is the optical path length.

3. The system of claim 2, wherein the at least one light ray comprises a first light ray with a first wavelength and a second light ray with a second wavelength, the at least one response light ray comprises a first response light ray and a second response light ray, and the calculation circuit is configured to calculate the concentration of the matter according to an equation (2), $$\frac{I_{\lambda_1}}{I_{\lambda_2}} = e^{(\varepsilon_{\lambda_1} - \varepsilon_{\lambda_2}) l \cdot x} \qquad (2)$$

wherein $I_{\lambda_1}$ is an intensity of the first response light ray, $I_{\lambda_2}$ is an intensity of the second response light ray, $\varepsilon_{\lambda_1}$ is a Molar absorption coefficient of the matter with respect to the first wavelength, $\varepsilon_{\lambda_2}$ is a Molar absorption coefficient of the matter with respect to the second wavelength, and x is the concentration of the matter.

4. The system of claim 3, wherein the at least one light source is an adjustable light source configured to emit the first light ray and the second light ray at different time according to a control signal.

5. The system of claim 2, wherein the at least one light ray has a first wavelength, and the calculation circuit is configured to calculate the concentration of the mater according to an equation (2), $$-\ln\frac{I_{\lambda_1}}{I_{o1}} = \varepsilon_{\lambda_1} \cdot l \cdot x \qquad (2)$$

wherein $I_{o1}$ is an intensity of the at least one light ray, $I_{\lambda_1}$ is an intensity of the at least one response light ray, $\varepsilon_{\lambda_1}$ is a Molar absorption coefficient of the matter with respect to the first wavelength, and x is the concentration of the matter.

6. The system of claim 2, wherein the at least one light ray has a first wavelength, the calculation circuit is configured to divide each element of the at least one Muller matrix by an element at a first column and a first row of the Muller matrix to obtain a normalized matrix and calculate an average absorbance according to the Muller matrix and the normalized matrix, wherein the calculation circuit is configured to calculate the concentration of the matter according to an equation (2), $$x = \frac{c_{\lambda_1} A e_{\lambda_1}}{\varepsilon_{\lambda_1} \cdot l} \qquad (2)$$

wherein $\varepsilon_{\lambda_1}$ is a Molar absorption coefficient of the matter with respect to the first wavelength, $c_{\lambda_1}$ is a ratio constant corresponding to the first wavelength, $Ae_{\lambda_1}$ is the average absorbance, and x is the concentration of the matter.

7. The system of claim 2, wherein the at least one light ray comprises a first light ray with a first wavelength and a second light ray with a second wavelength, the at least one Muller matrix comprises a first Muller matrix and a second Muller matrix, wherein the calculation circuit is configured to calculate two normalized matrices according to the first Muller matrix and the second Muller matrix so as to calculate an average absorbance corresponding to the first wavelength and an average absorbance corresponding to the second wavelength, the calculation circuit is configured to calculate the concentration of the matter according to an equation (2), $$x = \frac{c_{\lambda_1} A e_{\lambda_1} - c_{\lambda_2} A e_{\lambda_2}}{(\varepsilon_{\lambda_1} - \varepsilon_{\lambda_2}) \cdot l} \qquad (2)$$

wherein $\varepsilon_{\lambda_1}$ is a Molar absorption coefficient of the matter respect to the first wavelength, $\varepsilon_{\lambda_2}$ is a Molar absorption coefficient of the matter respect to the second wavelength, $c_{\lambda_1}$ is a ratio constant corresponding to the first wavelength, $c_{\lambda_2}$ is a ratio constant corresponding to the second wavelength, $Ae_{\lambda_1}$ is the average absorbance of the first wavelength, $Ae_{\lambda_2}$ is the average absorbance of the second wavelength, and x is the concentration of the matter.

8. The system of claim 1, wherein the matter is glycosylated hemoglobin or glucose.

9. A method for a system comprising a calculating circuit, the method comprising:

emitting, by at least one light source, at least one light ray which is configured to pass through a first polarization state changing module and then directed to a biological tissue to generate at least one response light ray which is configured to pass through a second polarization state changing module and then received by a sensor, wherein the first polarization state changing module comprises at least one first birefringent plat and at least one first linear polarizer, and the second polarization state changing module comprises at least one second birefringent plat and at least one second linear polarizer;

calculating at least one Muller matrix corresponding to the biological tissue according to the at least one response light ray;

calculating a depolarization index corresponding to the biological tissue according to the at least one Muller matrix;

calculating an optical path length according to the depolarization index; and calculating a concentration of a matter in the biological tissue according to the optical path length, wherein the matter is configured to absorb at least a portion of the at least one light ray, wherein the at least one light ray comprises a first light ray with a first wavelength and a second light ray with a second wavelength, the at least one response light ray comprises a first response light ray and a second response light ray, and the concentration of the matter is calculated according to a following equation, $$\frac{I_{\lambda_1}}{I_{\lambda_2}} = e^{(\varepsilon_{\lambda_1} - \varepsilon_{\lambda_2}) l \cdot x}$$

wherein $I_{\lambda_1}$ is an intensity of the first response light ray, $I_{\lambda_2}$ is an intensity of the second response light ray, $\varepsilon_{\lambda_1}$ is a Molar absorption coefficient of the matter with respect to the first wavelength, $\varepsilon_{\lambda_2}$ is a Molar absorption coefficient of the matter with respect to the second wavelength, and x is the concentration of the matter.

10. A method for a system comprising a calculating circuit, the method comprising:
    emitting, by a light source, a light ray which is configured to pass through a first polarization state changing module and then directed to a biological tissue to generate a response light ray which is configured to pass through a second polarization state changing module and then received by a sensor, wherein the first polarization state changing module comprises at least one first birefringent plat and at least one first linear polarizer, and the second polarization state changing module comprises at least one second birefringent plat and at least one second linear polarizer;
    calculating at least one Muller matrix corresponding to the biological tissue according to the response light ray;
    calculating a depolarization index corresponding to the biological tissue according to the at least one Muller matrix;
    calculating an optical path length according to the depolarization index; and
    calculating a concentration of a matter in the biological tissue according to the optical path length, wherein the matter is configured to absorb at least a portion of the light ray,
    wherein the light ray has a first wavelength, and the concentration of the matter is calculated according to a following equation, $$-\ln\frac{I_{\lambda_1}}{I_{o1}} = \varepsilon_{\lambda_1} \cdot l \cdot x$$

wherein $I_{o1}$ is an intensity of the light ray, $I_{\lambda_1}$ is an intensity of the response light ray, $\varepsilon_{\lambda_1}$ is a Molar absorption coefficient of the matter with respect to the first wavelength, and x is the concentration of the matter.

* * * * *